United States Patent
McDermott

(10) Patent No.: US 6,589,273 B1
(45) Date of Patent: Jul. 8, 2003

(54) APPARATUS AND METHOD FOR RELINING A BLOOD VESSEL

(75) Inventor: John D. McDermott, Mesa, AZ (US)

(73) Assignee: Impra, Inc., Tempe, AZ (US)

( * ) Notice: Subject to any disclaimer, the term of this patent is extended or adjusted under 35 U.S.C. 154(b) by 198 days.

(21) Appl. No.: 09/678,505

(22) Filed: Oct. 2, 2000

(51) Int. Cl.[7] ................................................ A61F 2/06
(52) U.S. Cl. ...................... 623/1.11; 623/1.13; 623/1.23; 606/108
(58) Field of Search ............................. 623/1.1, 1.11, 623/1.13, 1.23, 11, 12; 606/191–192, 194–195, 198, 108; 604/96.01, 104

(56) References Cited

U.S. PATENT DOCUMENTS

| | | |
|---|---|---|
| 4,681,110 A | 7/1987 | Wiktor |
| 4,998,539 A | 3/1991 | Delsanti |
| 5,071,407 A | 12/1991 | Termin et al. |
| 5,104,399 A * | 4/1992 | Lazarus .................... 623/1.14 |
| 5,275,622 A * | 1/1994 | Lazarus et al. ............. 623/1.11 |
| 5,397,345 A | 3/1995 | Lazarus |
| 5,405,380 A | 4/1995 | Gianotti et al. |
| 5,456,713 A | 10/1995 | Chuter |
| 5,562,725 A | 10/1996 | Schmitt et al. |
| 5,562,728 A | 10/1996 | Lazarus et al. |
| 5,569,295 A | 10/1996 | Lam |
| 5,571,135 A | 11/1996 | Fraser et al. |
| 5,571,168 A | 11/1996 | Toro |
| 5,578,072 A | 11/1996 | Barone et al. |
| 5,591,195 A | 1/1997 | Taheri et al. |
| 5,591,222 A | 1/1997 | Susawa et al. |
| 5,591,229 A | 1/1997 | Parodi |
| 5,662,675 A | 9/1997 | Polanskyj Stockert et al. |
| 5,662,700 A | 9/1997 | Lazarus |
| 5,662,701 A | 9/1997 | Plaia et al. |
| 5,669,936 A | 9/1997 | Lazarus |
| 5,749,920 A | 5/1998 | Quiachon et al. |
| 5,824,041 A * | 10/1998 | Lenker et al. .............. 606/195 |
| 5,836,316 A | 11/1998 | Plaia et al. |
| 5,843,165 A | 12/1998 | Plaia et al. |
| 5,879,380 A | 3/1999 | Kalmann et al. |
| 5,934,284 A | 8/1999 | Plaia et al. |
| 5,957,973 A | 9/1999 | Quiachon et al. |
| 6,174,330 B1 * | 1/2001 | Stinson ...................... 606/198 |
| 6,383,214 B1 * | 5/2002 | Banas et al. ............... 623/1.14 |
| 6,398,802 B1 * | 6/2002 | Yee ............................ 606/108 |

* cited by examiner

Primary Examiner—David J. Isabella
Assistant Examiner—Urmi Chattopadhyay
(74) Attorney, Agent, or Firm—Morrison & Foerster

(57) ABSTRACT

A delivery system and device for re-lining bodily vessels. A stent is attached to a distal end of a tubular lining made of biocompatible material and loaded into a hollow atraumatic tip. A semi-rigid shaft connects the atraumatic tip to a stopper and runs through the center of the tubular lining. The proximal end of the tubular lining is attached to a sliding hub. Optionally, a balloon is positioned near the stent in fluid communication with the shaft. The assembled device is introduced into a bodily vessel following an endarterectomy or atherectomy procedure. The atraumatic tip is delivered to a predetermined location and upon reaching that destination, the stent is released from the tip to expand against the vessel wall. If a balloon is utilized, it is inflated to ensure that the stent is fully deployed within the vessel. The balloon is then deflated arid the tip and shaft are pulled through the expanded stent and tubular lining. The sliding hub is cut off of the tubular lining and the proximal anastomosis is completed.

14 Claims, 3 Drawing Sheets

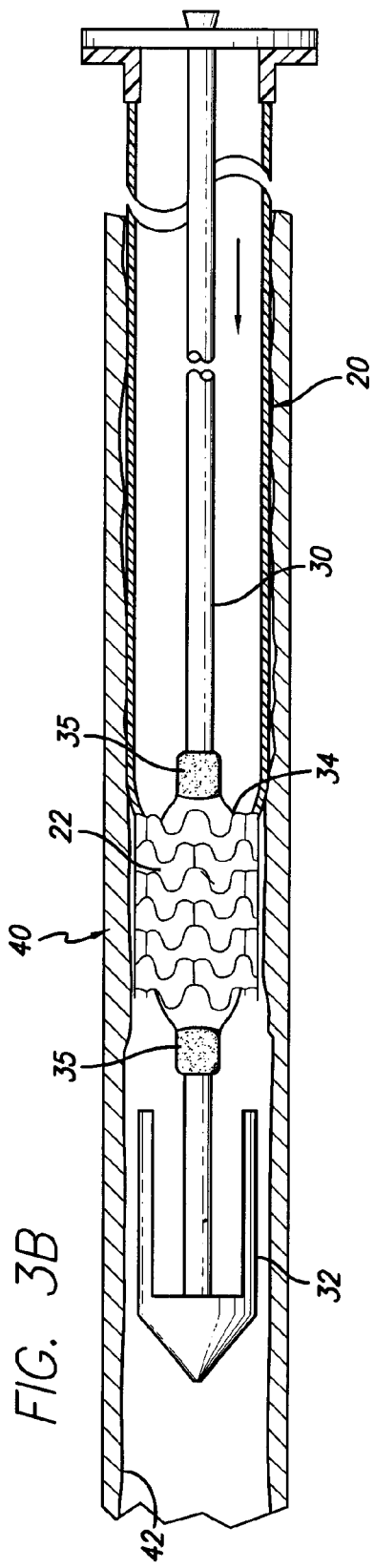
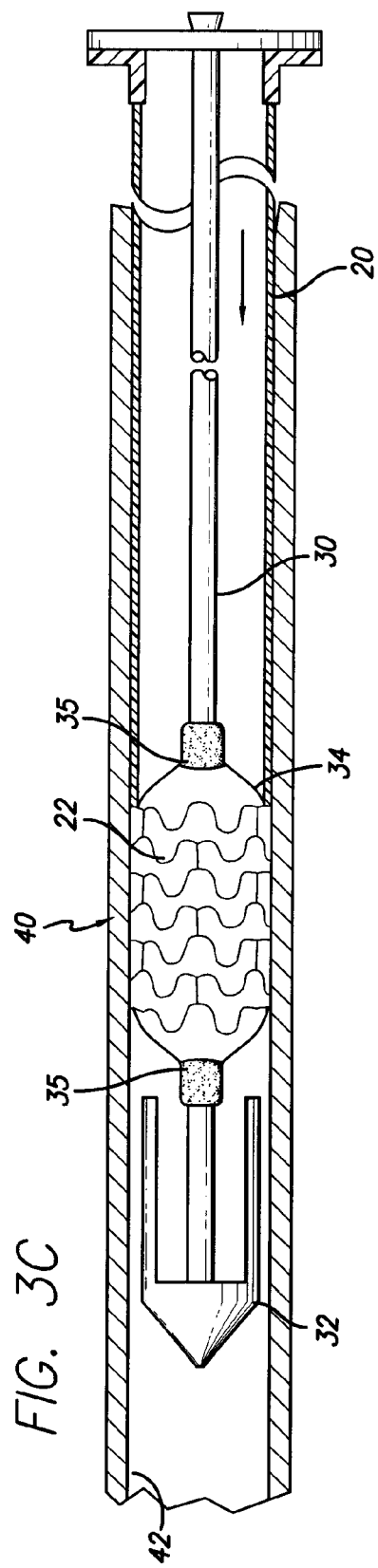
FIG. 3B
FIG. 3C

APPARATUS AND METHOD FOR RELINING A BLOOD VESSEL

BACKGROUND OF THE INVENTION

1. Field of the Invention

The present invention relates generally to the field of medical devices, and more particularly, to a graft to re-line a debulked vessel.

2. Description of Related Art

Arterial stenosis is a disease of the artery wherein a portion of the vessel becomes occluded, primarily with plaque (atheroma) containing cholesterol, lipid material, macrophages and proliferating smooth muscle cells, consequently restricting blood flow and causing further complications. Traditionally, arterial stenosis has been treated by surgical construction of a bypass channel to connect healthy parts of the vessel around the atheroma. While the bypass method may produce good results, a major disadvantage is the invasiveness of the surgery because the procedure requires general anesthesia and a substantial post-surgical healing period.

Another, less invasive method of treatment includes balloon catheter angioplasty, where a balloon catheter is inserted into the diseased portion of the vessel and inflated, pushing the atheroma outward and opening the vessel. While balloon catheter angioplasty is much less invasive than bypass surgery, it does not enjoy similar success rates due to frequent restenosis of the vessel. To overcome this problem, stents and other similar endoluminal devices may be inserted to keep the vessel open following angioplasty. Cellular infiltration through the stents' mesh-like structure makes the use of bare stents less than optimal, particularly in longer (>5 cm) legions. Consequently, the stent may be covered with a biocompatible material such as polytetrafluoroethylene (PTFE) to prevent cellular infiltration.

Endarterectomy is a method for treating occluded portions of a vessel where the atheroma is surgically removed, along with the inner two layers (intima and media) of the three-layered artery. Following the endarterectomy, only the adventitia layer remains, thus the vessel can be prone to cellular accumulation and thrombosis.

Artherectomy is a method for treating occluded blood vessels where a mechanical device is inserted into the vessel, removing atheroma by cutting or grinding the plaque and creating an open channel. Similar to endarterectomy, this procedure can trigger a cellular response that leads to thrombosis and/or restenosis of the vessel.

Another term for endarterectomy and artherectomy is "debulking." Debulking is simply the removal of atheroma, plaque and other tissue to restore blood flow in a vessel. To prevent the cellular response that leads to thrombosis and/or restenosis following a debulking procedure, the vessel can be re-lined with PTFE or other biocompatible materials.

Many delivery systems have been used for introducing stents, grafts, and other endoluminal devices into bodily vessels with minimum invasiveness. One problem with a number of these systems, however, is that they require multiple components and procedural steps to deliver and deploy the device against the vessel wall. In addition, grafts and -other endoluminal devices used to currently re-line vessels are not optimal due to problems with effectively anchoring the device within the vessel.

The present invention overcomes these stated drawbacks by providing a simple delivery system and device to re-line a vessel following debulking.

SUMMARY OF THE INVENTION

The present invention is directed to a delivery system and device for re-lining blood vessels. In particular, following debulking procedures, a graft containing a stent or other fixation device is deployed slightly distal to the debulked section of the vessel. A small balloon on the shaft of the delivery catheter is inflated to ensure good opposition of the graft to the vessel wall. Next, the delivery system is removed through the newly implanted graft, which is sutured proximally to the debulked vessel.

It is an object of this invention to provide an endoluminal vascular graft device to re-line a debulked vessel as a less invasive alternative to traditional surgical bypass.

It is another object of this invention to provide an endoluminal vascular graft device that has a minimal profile when loaded into an insertion system, can be seen with fluoroscopic imaging and can be deployed quickly and easily.

It is yet another object of this invention to provide a delivery system to introduce the endoluminal vascular graft device quickly, easily and effectively within the debulked vessel.

These and additional objects are accomplished by delivering a graft with an attached stent or other support structure to a debulked vessel. The replacement lining is delivered to the desired site by, using a delivery system, including an atraumatic tip to house the stent, a sliding hub attached to the graft lining material, and an inner shaft connected to the tip.

To prepare the replacement lining for delivery, the distal stent is bonded, attached or encapsulated to the graft material. The graft material can either be supported, unsupported, or a combination of the two to resist compression. The distal portion is compressed into the atraumatic tip for delivery to the desired site within the treated vessel. Ideally, a self-expanding stent is used for this purpose so that the deployment of the stent occurs quickly, as soon as it is released from the atraumatic tip, thus ensuring that the stent can be deployed at the pre-selected location without migration in either direction within the vessel.

The atraumatic tip is connected to an inner shaft that extends through the compressed stent and graft material to the proximal end of the delivery device. The connection between the tip and the shaft allows the device to be maneuvered as it is being inserted into the vessel. Optionally coupled to the shaft, proximal to the loaded stent, is a balloon that is positioned to be inside of the stent after the stent is removed from the atraumatic tip. Once the stent is removed from the atraumatic tip and expands to come into contact with the vessel wall, the balloon can be inflated to ensure a good fit to the vessel wall. A sliding hub is attached to the proximal end of the graft lining material so that the distal stent can be pulled out of the atraumatic tip. After the delivery system is removed from the vessel and the graft lining material is pulled taut, the sliding hub is cut off of the graft lining material and the lining material is sutured to the treated vessel.

A more complete understanding of the endoluminally placed vascular graft and delivery system will be afforded to those skilled in the art, as well as a realization of additional advantages and objects thereof, by a consideration of the following detailed description of the preferred embodiment; Reference will be made to the appended sheets of drawings, which will first be described briefly.

BRIEF DESCRIPTION OF THE DRAWINGS

FIG. 3B is cross-sectional view of the present invention after the stent has been deployed from the atraumatic tip.

FIG. 3C is a cross-sectional view of the present invention as the stent is tightly fit to the vessel wall.

DETAILED DESCRIPTION OF THE INVENTION

The present invention satisfies the need for a replacement lining for a vessel and a method of delivering the lining to a desired location. This is accomplished by bonding, attaching or encapsulating a stent at one end of a biocompatible plastic lining material and loading the stent and lining into a delivery system including an atraumatic tip, a sliding hub and an inner shaft with a balloon.

Figure 1:
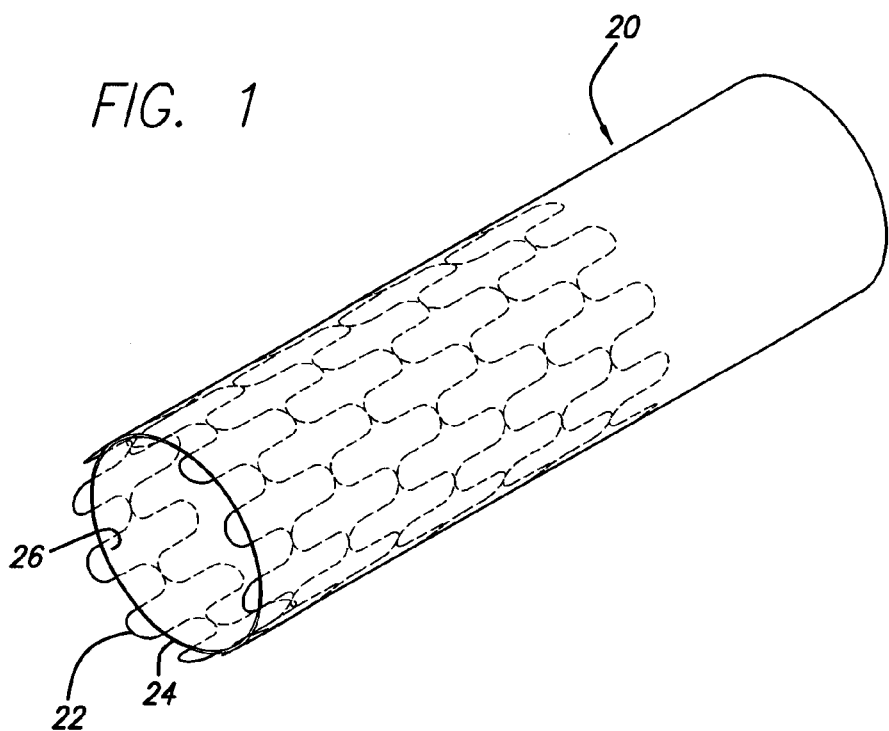
FIG. 1 is a perspective view of a distal end of the vascular graft device after it has been deployed from the catheter.

Referring now to the drawings, in which like reference numbers represent similar or identical structures throughout, FIG. 1 illustrates a preferred embodiment of the replacement lining of the present invention. A distal end of a replacement lining 20 is shown with a shadow view of a stent 22 attached thereto. The stent 22 may be attached to the lining 20 at its distal end in any number of ways including, but not limited to, direct bonding, bonding with the use of an adhesive material, and encapsulation with the use of an additional tubular portion of ePTFE. The stent 22 can be attached to the luminal or abluminal surface of the lining, or in the case of encapsulation, the stent can have the lining as its luminal or abluminal surface. The lining is a biocompatible graft material, which in the preferred embodiment is expanded polytetrafluoroethylene (ePTFE). The preferred ePTFE is one optimized for bond strength as described in U.S. Pat. No. 5,749,880, incorporated by reference, herein. In FIG. 1, the stent 22 is self-expanding, thus not requiring any external force to conform to the sides of the vessel wall in which it is placed. However, many other stent configurations are possible, including various self-expanding and balloon expandable stents.

FIG. 1 shows encapsulation of the stent 22 as the attachment method to the lining 20. The stent 22 is encapsulated between two layers of ePTFE 24 and 26 by utilizing a mandrel assembly. Once the appropriate ePTFE coverings are placed onto the luminal and abluminal surfaces, the stent 22 is encapsulated within the replacement lining 20 at the lining's distal end by connecting or bonding the luminal covering 26 to the abluminal covering 24. The replacement lining 20 represents the continuation of the ePTFE covering whether it be a continuation of the abluminal covering 24 from the stent to the proximal end of the device 10 (see FIG. 2), the luminal covering 26, or both luminal and abluminal coverings 24 and 26. Encapsulation can be accomplished by a number of methods as is well-known in the art.

Figure 2:
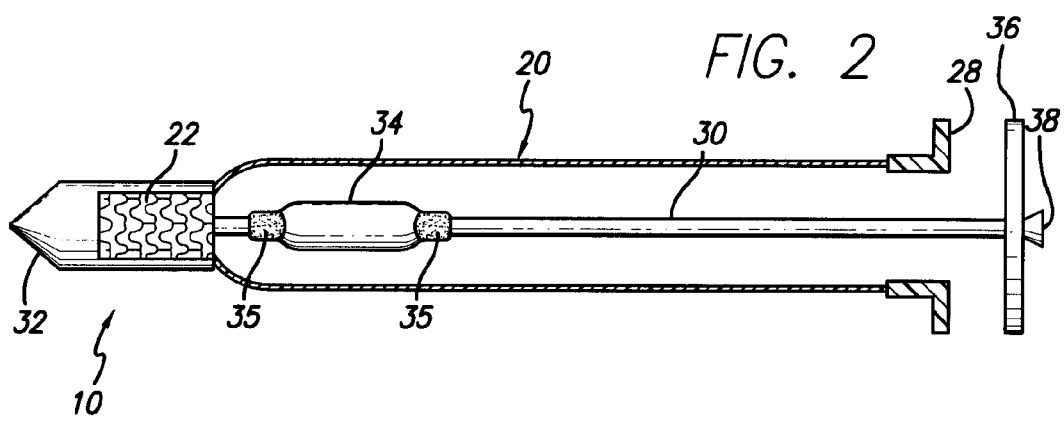
FIG. 2 is a cross-sectional view of a preferred embodiment of the vascular graft device and delivery system of the present invention.

FIG. 2 illustrates a cross-section of the delivery system 10 containing the replacement lining 20 before introduction into the vessel of a patient The delivery system 10 contains an atraumatic tip 32 that encloses the stent 22 in a small-diameter state, after it has been reduced in size by any of the known loading methods, including the method disclosed in U.S. Ser. No. 09/310,763, which is incorporated by reference herein. Attached to the atraumatic tip 32, extending the length of the delivery system 10, is a shaft 30 that connects the tip 32 to a stopper 36. Built into the stopper 36 is a hub 38 for the inflation of an optional balloon 34 located proximally a short distance from the loaded stent 22 along the shaft 30. The optional balloon 34 has radiopaque markers 35 situated at both ends to reveal the proximal and distal ends of the balloon 34 to assist in the positioning of the balloon 34 with respect to the stent 22. The stent 22 is attached to the biocompatible replacement lining 20 at the distal end thereof. As is evident from the drawing, the lining 20 has a length greater than the length of the stent 22. At the proximal end of the replacement lining 20, a sliding hub 28 is attached to the lining 20 to pull back the replacement lining 20 from the atraumatic tip 32 and deploy the stent 22 and replacement lining 20 within a vessel. The stopper 36 has a diameter greater than the diameter of the lining 20 to prevent bitter movement thereof in a proximal direction during deployment of the stent 20.

Figure 3A:
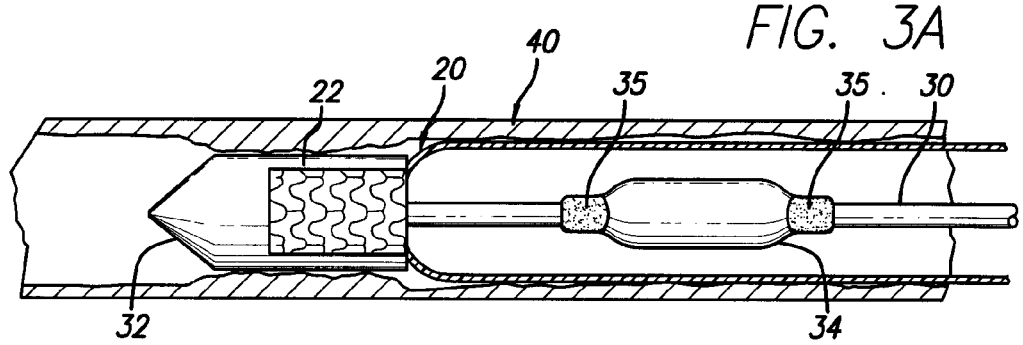
FIG. 3A is a cross-sectional-view of the present invention being delivered in vivo.

FIGS. 3A through 3D illustrate the replacement lining 20 as it is deployed within a vessel 40. In FIG. 3A, the delivery system 10 is introduced into the vessel 40 through a single entry point (not shown), distal to the end of the endarterectomy or atherectomy, in which the replacement lining 20 is to be implanted. The delivery system 10 can be manipulated through the vessel 40 by the stopper 36 due to the rigidity of the shaft 30, which is connected proximally to the stopper 36 and distally to the atraumatic tip 32 (shown in FIG. 2). In order to monitor the device 10 as it is guided through the treated vessel 40, markers can be placed on or encapsulated within the replacement liner 20, on the stent 22, and/or on the optional balloon 34 (as shown in FIGS. 2–4) when included as a part of the device 10. Once the device 10 has reached the desired location within the vessel 40, the stent 22 is removed from the atraumatic tip 32 and deployed within the vessel 40 as shown in FIG. 3B.

Referring again to FIG. 2, the deployment of the stent 22 is preferably accomplished by holding the stopper 36 steady while pulling the sliding hub 28, attached to lining 20, toward the stopper 36. This action pulls the stent 22 attached to a distal end of the lining 20 out of the atraumatic tip 32, allowing the stent 22 to self-expand to its pre-loaded diameter to bring it and the attached lining 20 in close proximity to the vessel wall 42. (Alternatively, the stopper 36 can be pushed toward the sliding hub 28 while the hub is held steady, thereby pushing the atraumatic tip 32 off of the stent 22)The optional balloon 34, when present, is positioned proximal to the stent 22 so that removal of the stent 22 from the atraumatic tip 32 places the expanding stent 22 over the top of the balloon 34 as shown in FIG. 3B. The balloon is 34, which is then within the lumen created by the stent 22 as the stent 22 expands close to the vessel wall 42, can be inflated to come into contact with the stent 22 as shown in FIG. 3C, thus ensuring a tight fit to the vessel wall 42.

Figure 3D:
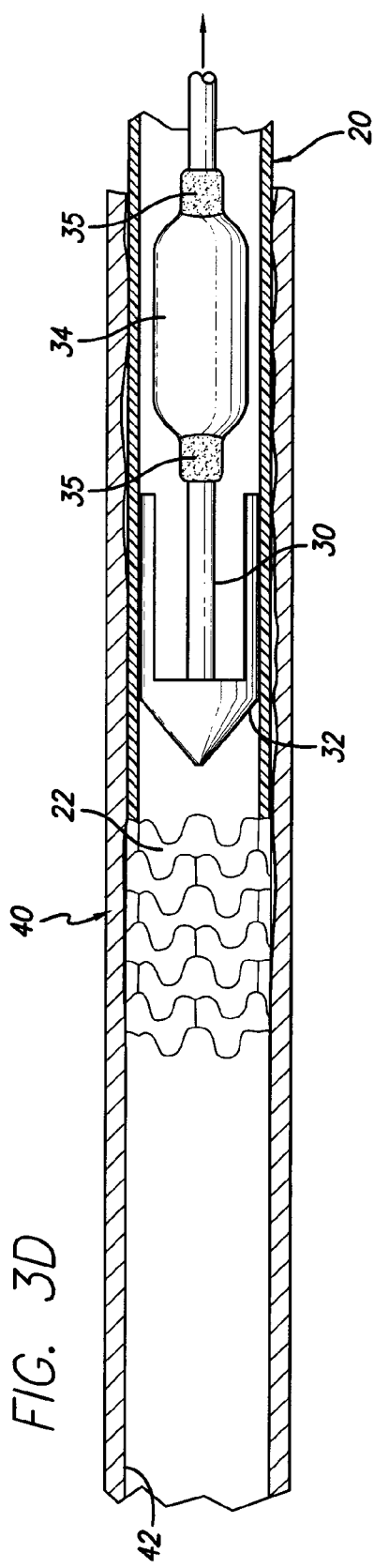
FIG. 3D is a cross-sectional view of the present invention as the delivery system is being removed from inside the replacement lining.
Figure 4:
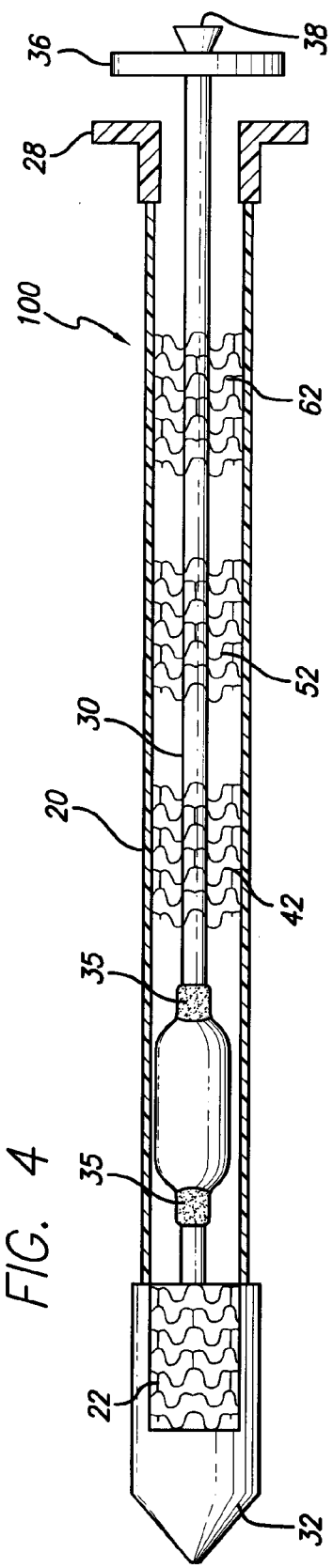
FIG. 4 is a cross-sectional view of an alternate embodiment of the present invention.

Referring to FIG. 3D, once the replacement lining 20 has been implanted within the vessel 40, the delivery system 10 is withdrawn from the vessel 40 through the replacement lining 20. The stopper 36, with atraumatic tip 32 in tow, is pulled through the lining 20 and out of the single incision site (not shown). Prior to removing the delivery system 10, the sliding hub 28 is detached from the lining 20 by cutting the lining material near the hub 28. The remaining lining material is then surgically attached to the vessel 40 wall through suturing or other accepted medical procedures, thus completing the proximal anastomosis.

FIG. 4 illustrates an alternate embodiment of the vascular graft device and delivery system of the present invention. In this embodiment, a delivery system 100 contains many of the same features as those of the delivery system 10 shown in FIG. 2, including the atraumatic tip 32, the shaft 30 that connects the atraumatic tip 32 to the stopper 36, and the balloon 34. In this embodiment, however, in addition to the stent 22 that is initially constrained within the atraumatic tip 32, there are several small balloon-expandable stents 42, 52, and 62 located at axially spaced apart intervals along the replacement lining 20. These stents can be expanded by the balloon 34 as it is withdrawn in a proximal direction. Only those areas requiring such support need to have a stent expanded in the corresponding location in the replacement lining 20. Thus, any vessel irregularity can be tailored according to stents that are expanded. It should be appreciated that any number of stents can be placed along the replacement lining 20. By having numerous stents placed at spaced apart intervals, the physician is permitted great flexibility in tailoring the present invention to each individual procedure.

Having thus described a preferred embodiment of the endoluminally placed vascular graft, it will be apparent by those skilled in the art how certain advantages of the present invention have been achieved. It should also be appreciated that various modifications, adaptations, and alternative embodiments thereof may be made. For example, while replacement linings with ePTFE have been illustrated, it should be apparent that the inventive concepts described herein would be equally applicable to other types of biocompatible covering materials. Moreover, the words used in this specification to describe the invention and its various embodiments are to be understood not only in the sense of their commonly defined meanings, but to include by special definition in this specification structure, material or acts beyond the scope of the commonly defined meanings. The definitions of the words or elements of the following claims are, therefore, defined in this specification to include not only the combination of elements which are literally set forth, but all equivalent structure, material or acts for performing substantially the same function in substantially the same way to obtain substantially the same result. The described embodiments are to be considered illustrative rather than restrictive. The invention is further defined by the following claims.

I claim:

1. In combination, an apparatus and delivery system for relining a blood vessel, comprising:

a tubular liner of biocompatible material having a proximal end and a distal end, wherein an anchoring stent is attached to said distal end of said liner for anchoring said liner within said blood vessel, and wherein a removable hub is attached to said proximal end of said tubular liner, said liner having a length greater than the length of said stent, wherein said proximal end of said liner in configured to be secured to said blood vessel following removal of said hub; and a hollow atraumatic tip positioned at a distal end of said delivery system, said tip being connected to a proximal end of said delivery system by a shaft, wherein said shaft is positioned within said liner, and wherein at least a portion of said stent is positioned within said tip.

2. The apparatus and delivery system according to claim 1, further comprising a stopper connected to said shaft at said proximal end of said delivery system, said stopper having a diameter that is greater than a diameter of said liner.

3. The apparatus and delivery system according to claim 1, further comprising a balloon and a balloon hub, wherein said balloon hub is positioned at a proximal end of said delivery system and is connected to said shaft, wherein said balloon is positioned around said shaft and in fluid communication therewith, said shaft comprising a passageway connecting said balloon to said balloon hub.

4. The apparatus and delivery system according to claim 1, further comprising location marking means.

5. The apparatus and delivery system according to claim 4, wherein said location marking means is positioned on said stent.

6. The apparatus and delivery system according to claim 4, wherein said location marking means is positioned on said liner.

7. The apparatus and delivery system according to claim 4, wherein said location marking means comprises a radiopaque material.

8. The apparatus and delivery system according to claim 3, wherein said balloon further comprises location marking means.

9. The apparatus and delivery system according to claim 8, wherein said location marking means comprises radiopaque material on a proximal and distal end of said balloon.

10. The apparatus and delivery system according to claim 1, wherein said biocompatible material is expanded polytetrafluoroethylene.

11. The apparatus and delivery system according to claim 1, wherein said anchoring stent is a self-expanding stent.

12. The apparatus and delivery system according to claim 1, wherein said liner further comprises a luminal layer and an abluminal layer, and wherein said stent is encapsulated between said luminal and abluminal layers.

13. The apparatus and delivery system according to claim 1, further length of said liner.

14. The apparatus and delivery system according to claim 3, further positioned along the length of said liner.

* * * * *